United States Patent
Kersey et al.

(10) Patent No.: US 12,326,404 B2
(45) Date of Patent: Jun. 10, 2025

(54) METHOD AND SYSTEM FOR DETECTING CANCEROUS TISSUE AND TUMOR MARGIN USING RAMAN SPECTROSCOPY

(71) Applicant: CytoVeris Inc., Farmington, CT (US)

(72) Inventors: Alan Kersey, South Glastonbury, CT (US); Rishikesh Pandey, Unionville, CT (US)

(73) Assignee: CytoVeris, Inc., Farmington, CT (US)

( * ) Notice: Subject to any disclaimer, the term of this patent is extended or adjusted under 35 U.S.C. 154(b) by 859 days.

(21) Appl. No.: 17/427,391

(22) PCT Filed: Jan. 31, 2020

(86) PCT No.: PCT/US2020/016196
§ 371 (c)(1),
(2) Date: Jul. 30, 2021

(87) PCT Pub. No.: WO2020/160462
PCT Pub. Date: Aug. 6, 2020

(65) Prior Publication Data
US 2022/0099580 A1     Mar. 31, 2022

Related U.S. Application Data

(60) Provisional application No. 62/874,694, filed on Jul. 16, 2019, provisional application No. 62/799,233, filed on Jan. 31, 2019.

(51) Int. Cl.
*B01L 3/00*   (2006.01)
*B01F 33/302*   (2022.01)
(Continued)

(52) U.S. Cl.
CPC ......... *G01N 21/658* (2013.01); *G01N 33/574* (2013.01); *G01N 33/587* (2013.01)

(58) Field of Classification Search
CPC .. G01N 21/658; G01N 33/574; G01N 33/587; B82Y 30/00; A61B 5/0075; A61K 49/001
See application file for complete search history.

(56) References Cited

U.S. PATENT DOCUMENTS

2010/0284917 A1   11/2010   Küstner
2013/0149247 A1   6/2013    Qian
(Continued)

OTHER PUBLICATIONS

Potara et al. "Carboplatin-Loaded Raman-Encoded, Chitosan-Coated Silver Nanotriangles as Multimodal Traceable Nanotherapeutic Delivery Systems and pH Reporters Inside Human Ovarian Cancer Cells", Applied Materials & Interfaces, vol. 9, No. 38, Sep. 13, 2017, pp. 32565-32576.

(Continued)

*Primary Examiner* — Jennifer Wecker
*Assistant Examiner* — Oyeleye Alexander Alabi
(74) *Attorney, Agent, or Firm* — Getz Balich LLC (57) ABSTRACT

A method and system for determining the presence or absence of cancerous cells within subject tissue. The method includes: providing a material that includes a peptide component configurable in a non-binding form when disposed in a neutral pH environment, and in a binding form when disposed in an acidic pH environment, wherein the peptide component is configured to produce a first Raman spectrum when subjected to one or more predetermined wavelengths of light; administering the material to a subject tissue; interrogating the subject tissue with light; sensing the subject tissue for light emitted from the subject tissue, and producing signals representative of the sensed emitted light; analyzing the signals to determine a presence or absence of the first Raman spectrum; and determining the presence or absence of cancerous cells based on the presence or absence of the first Raman spectrum within the sensed light emitted from the subject tissue.

13 Claims, 6 Drawing Sheets

(51) Int. Cl.
    *B01F 33/3033*  (2022.01)
    *B01L 7/00*     (2006.01)
    *C12Q 1/6848*   (2018.01)
    *C12Q 1/686*    (2018.01)
    *G01N 21/29*    (2006.01)
    *G01N 21/65*    (2006.01)
    *G01N 33/574*   (2006.01)
    *G01N 33/58*    (2006.01)

(56)  References Cited

U.S. PATENT DOCUMENTS

2014/0193837 A1   7/2014  Zheng
2015/0191508 A1   7/2015  Reshetnyak
2015/0192590 A1   7/2015  Sodeoka

OTHER PUBLICATIONS

EP search report for EP20747693.8 dated Oct. 19, 2022.
Antosh et al. "Enhancement of Radiation Effect on Cancer Cells by Gold-pHLIP", Proceedings of the National Academy of Sciences USA, Apr. 28, 2015, vol. 112, iss. 17, pp. 5372-5376.
Kohout et al. "Anisotropic Gold Nanoparticles in Biomedical Applications", International Journal of Molecular Science, Oct. 29, 2018, vol. 19, iss. 11, pp. 1-30.
Li et al. "Raman Tags: Novel Optical Probes for Intracellular Sensing and Imaging", Biotechnology Advances, Dec. 23, 2016, vol. 35, iss. 2, pp. 168-177.
Wyatt et al. "Applications of pHLIP Technology for Cancer Imaging and Therapy", Trends in Biotechnology, Apr. 21, 2017, vol. 5, iss. 7, pp. 653-664.

METHOD AND SYSTEM FOR DETECTING CANCEROUS TISSUE AND TUMOR MARGIN USING RAMAN SPECTROSCOPY

This application is a national stage application of PCT/US2020/016196 filed Jan. 31, 2020, which claims priority to U.S. Patent Appln. Nos. 62/799,233 filed Jan. 31, 2019, and 62/874,694 filed Jul. 16, 2019, all of which are incorporated by reference herein in their entirety.

BACKGROUND OF THE INVENTION

1. Technical Field

The present disclosure relates to systems and methods for the detection and identification of cancerous/precancerous tissue, and more specifically systems and methods for the detection and identification of cancerous tissue using Raman spectroscopy.

2. Background Information

For many decades the reference method for the diagnosis of cancer has been histopathological examination of tissues using conventional microscopy. This process is known as Surgical Pathology. In Surgical Pathology, samples can be produced from surgical procedures (e.g., such as tumor resection surgery), diagnostic biopsies or autopsies. These samples go through a process that includes dissection, fixation, and cutting of tissue into precisely thin slices which are stained for contrast and mounted onto glass slides. The slides are examined by a pathologist under a microscope, and their interpretations of the tissue results in the pathological "read" of the sample.

Current surgical techniques to resect cancer are limited by the lack of a precise method to determine the boundary between normal and cancerous cells/tissue, known as the 'tumor margin', in real time during surgical procedures. As a result, the success of such surgical procedures relies on the experience and judgement of the surgeon to decide on how much tissue to remove around the tumor. As a result, surgeons often perform what is called cavity shaving to increase the likelihood that all cancer is removed, which can result in the removal of excessive amounts of healthy tissue. Conversely, if the entire tumor is not removed during the initial surgery, a follow up surgery may be required to remove residual cancer tissue. In Breast Conserving Surgery, this is particularly an issue as the surgeon is balancing the two demands of the procedure: 1) remove all the tumor to avoid potential follow-on re-excision surgery, and 2) minimize the amount of health tissue remove to ensure good cosmetic outcomes. Any additional surgery required not only represents an additional economic burden to the healthcare system, but importantly, can be traumatic to the cancer patient, adding stress, resulting in long-term detrimental effects on the patient outcome.

Advanced optical and other electromagnetic imaging approaches have been reported for the determination of tumor margin: These include the use of fluorescence imaging (e.g., See [1], [2]), near infrared spectroscopy (e.g., See [3]), Raman spectroscopy (e.g., See [4]-[8]), and terahertz reflectivity (e.g., See [9]). The use of mass spectrometry to profile tumor/normal tissue boundaries has also been reported; e.g., a mass spectrometer coupled to a "pen" that allows testing of tumor tissue by determination and differentiation of indicators of cancerous tissue, such as, for example, the metabolites produced by cancer cells compared to normal tissue (e.g., See [10], [11]).

It is known that all tumors exhibit an acidic microenvironment, largely due to the due to glycolytic metabolic processes exhibited by cancer cells. To maintain rapid growth and proliferation, cancer cells have a higher need for energy which is to a large degree fulfilled by an increased dependence on alternate metabolic pathways. Under aerobic conditions, cancer cells metabolize glucose to lactic acid, a process generally called the Warburg effect (e.g., See [12]). Tumor tissue is also generally hypoxic (lacking in oxygen), has deficient blood perfusion, and has lower glucose levels (e.g., See [13]). Generally, these characteristics result in a microenvironment is pH of 6.4 to 6.8, whereas the surrounding normal tissue is close to neutral pH (7.2). The extracellular microenvironment acidity of cancer is associated with tumor progression and tumor metastasis (e.g., See [13], [14]).

Several approaches that aim to utilize this effect of low pH tumor microenvironment to allow targeted delivery of drugs to tumor sites have been explored, including pH sensing peptides (e.g., See [15], [16]), other peptides (e.g., See [17]), nanoparticles (e.g., See [18]), tumor cell-surface marker targeting (e.g., See [19]), etc. The pH sensing peptide, called pH (low) insertion peptide (pHLIP) is based on an amino acid sequence that reversibly folds and can insert across cell membranes in response to local intra-cellular low pH conditions. This folding of the pHLIP occurs due the increased hydrophobicity of the peptide in low pH environments; consequently, the pHLIP peptide has proven itself as a versatile mechanism to target acidic tissue, and thus to image tumors via a variety of imaging modalities. The markers for imaging have included optical fluorescence markers, and PET image contrast enhancement markers (e.g., see [20]). These approaches have also, in part, leveraged pH sensitive fluorescent dyes, such as Seminaphtharhodafluor (SNARF) dyes (e.g., See [21]) that change in their optical emission spectrum depending on the pH of the surrounding media/environment.

SUMMARY

According to one aspect of the present disclosure, a method for determining the presence or absence of cancerous cells within subject tissue is provided. The method includes: providing a material that includes at least one type of peptide component configurable in a non-binding form when disposed in a neutral pH environment, and in a binding form when disposed in an acidic pH environment, wherein the peptide component is configured to produce a first Raman spectrum when subjected to one or more predetermined wavelengths of light; administering the material to a subject tissue; interrogating the subject tissue with light at the one or more predetermined wavelengths of light produced by one or more light sources; sensing the subject tissue for light emitted from the subject tissue using one or more light detectors, the emitted light resulting from the light interrogation of the subject tissue, and producing signals representative of the sensed emitted light; analyzing the signals representative of the sensed emitted light using an analyzer to determine a presence or absence of the first Raman spectrum produced by the peptide component when subjected to one or more predetermined wavelengths of light; and determining the presence or absence of cancerous cells within the subject tissue based on the presence or absence of the first Raman spectrum within the sensed light emitted from the subject tissue.

In any of the aspects or embodiments described above and herein, the method may include a step of washing the subject tissue after an incubation period to remove any unbound peptide components.

In any of the aspects or embodiments described above and herein, the interrogating step may be performed after an incubation period, which incubation period is sufficient for some number of the peptide components to bind with any cancerous cells present, and for unbound peptide components to withdraw from the subject tissue.

In any of the aspects or embodiments described above and herein, the peptide component may include a pH (low) insertion peptide (pHLIP) and a Raman Reporter (RR), the RR configured to produce the first Raman spectrum when subjected to the one or more predetermined wavelengths of light, and the first Raman spectrum is distinguishable from Raman spectra produced by the subject tissue when subjected to the one or more predetermined wavelengths of light.

In any of the aspects or embodiments described above and herein, the first Raman spectrum may reside within a Raman silent region defined by a wavelength region within a range of about 1800 $cm^{-1}$ to about 2800 $cm^{-1}$.

In any of the aspects or embodiments described above and herein, an RR may include at least one of an alkyne, a nitrile, or an azide moiety.

In any of the aspects or embodiments described above and herein, the step of sensing the subject tissue for light emitted from the subject tissue using one or more light detectors may include filtering the signals representative of the sensed emitted light through one or more narrow-pass band filters configured to permit passage of only those signals representative of the first Raman spectrum within the Raman silent region.

In any of the aspects or embodiments described above and herein, the steps of sensing and analyzing may be performed without a spectral analysis device.

In any of the aspects or embodiments described above and herein, an RR may include at least one surface enhanced Raman spectroscopic (SERS) material.

In any of the aspects or embodiments described above and herein, a SERS material may include at least one of gold or silver.

In any of the aspects or embodiments described above and herein, a SERS material may include at least one of platinum, ruthenium, palladium, iron, cobalt, nickel, lithium, sodium, potassium, rubidium, or copper.

In any of the aspects or embodiments described above and herein, the peptide component may include a pH (low) insertion peptide (pHLIP), and the pHLIP is configurable in the non-binding form or the binding form, and in the binding form the pHLIP may produce the first Raman spectrum when subjected to one or more predetermined wavelengths of light, and the first Raman spectrum is distinguishable from Raman spectra produced by the subject tissue when subjected to the one or more predetermined wavelengths of light.

In any of the aspects or embodiments described above and herein, the peptide component may include a pH (low) insertion peptide (pHLIP), and the pHLIP may produce the first Raman spectrum when subjected to one or more predetermined wavelengths of light, and the first Raman spectrum is distinguishable from Raman spectra produced by the subject tissue when subjected to the one or more predetermined wavelengths of light.

According to another aspect of the present disclosure, a system for determining the presence or absence of cancerous cells within subject tissue is provided. The system includes: a material that includes at least one type of peptide component configurable in a non-binding form when disposed in a neutral pH environment, and in a binding form when disposed in an acidic pH environment, wherein the peptide component is configured to produce a first Raman spectrum when subjected to one or more predetermined wavelengths of light; at least one light source configured to interrogate a subject tissue with light at the one or more predetermined wavelengths of light; at least one light detector configured to detect light emitted from the subject tissue, the emitted light resulting from the light interrogation of the subject tissue, and configured to produce signals representative of the detected emitted light; and an analyzer in communication with the at least one light source, the at least one light detector, and a non-transitory memory storing instructions, which instructions when executed cause the analyzer to: control the at least one light source to interrogate subject tissue with the light at the one or more predetermined wavelengths of light, the subject tissue administered with the material; receive the signals representative of the detected emitted light from the at least one light detector; analyze the signals to determine a presence or absence of the first Raman spectrum; and determine the presence or absence of cancerous cells within the subject tissue based on the presence or absence of the first Raman spectrum within the sensed light emitted from the subject tissue.

In any of the aspects or embodiments described above and herein, the peptide component may include a pH (low) insertion peptide (pHLIP) and a Raman Reporter (RR), the RR configured to produce the first Raman spectrum when subjected to the one or more predetermined wavelengths of light, and the first Raman spectrum is distinguishable from Raman spectra produced by the subject tissue when subjected to the one or more predetermined wavelengths of light.

In any of the aspects or embodiments described above and herein, the first Raman spectrum may reside within a Raman silent region defined by a wavelength region within a range of about 1800 $cm^{-1}$ to about 2800 $cm^{-1}$.

In any of the aspects or embodiments described above and herein, an RR may include at least one of an alkyne, a nitrile, or an azide moiety.

In any of the aspects or embodiments described above and herein, the system may further include one or more narrow-pass band filters configured to permit passage of only those signals representative of the first Raman spectrum within the Raman silent region.

In any of the aspects or embodiments described above and herein, the analyzer may be configured to determine the presence or absence of cancerous cells within the subject tissue without a spectral analysis device based on the presence or absence of the first Raman spectrum within the sensed light emitted from the subject tissue.

In any of the aspects or embodiments described above and herein, a peptide component may include a pH (low) insertion peptide (pHLIP), and the pHLIP is configurable in the non-binding form or the binding form, and in the binding form the pHLIP produces the first Raman spectrum when subjected to one or more predetermined wavelengths of light, and the first Raman spectrum is distinguishable from Raman spectra produced by the subject tissue when subjected to the one or more predetermined wavelengths of light.

In any of the aspects or embodiments described above and herein, a peptide component may include a pH (low) insertion peptide (pHLIP), and the pHLIP produces the first Raman spectrum when subjected to one or more predetermined wavelengths of light, and the first Raman spectrum is distinguishable from Raman spectra produced by the subject tissue when subjected to the one or more predetermined wavelengths of light.

The foregoing features and elements may be combined in various combinations without exclusivity, unless expressly indicated otherwise. These features and elements as well as the operation thereof will become more apparent in light of the following description and the accompanying drawings. It should be understood, however, the following description and drawings are intended to be exemplary in nature and non-limiting.

DETAILED DISCLOSURE

As will be described below, the present disclosure method and system provide a means for determining the presence or absence of cancerous cells/tissue. If the presence of cancerous cells/tissue is determined, the present disclosure method and system can be used to locate the cancerous cells/tissue and importantly determine boundaries (i.e., the tumor margin) between non-cancerous tissue and cancerous tissue.

The present disclosure advantageously leverages Raman light scattering characteristics of certain materials for determining the presence or absence of cancerous cells/tissue. Raman light scattering refers to inelastic scattering in a material where there is an exchange of energy between the incident photons and the vibrational energy levels of the molecular bonds present in the material. All materials exhibit Raman scattering in response to incident light. The Raman spectrum for a given material is typically complex due to the variety of molecular bonds present within the material, and the material is identifiable based on the Raman spectrum. An exemplary Raman spectrum may include a number of different peaks at a certain wavelengths or 'wavenumber' offsets from the incident light, which are uniquely characteristic of the material. Hence, the Raman spectrum of a particular material can be thought of as a "fingerprint" or "signature" of that particular material, and can be used for identification purposes. Human tissue has a particularly complex Raman spectrum, and the differences in the Raman spectrum associated with normal and diseased tissue can be subtle, but reproducible. The present disclosure provides a methodology for enhancing the distinguishability between normal and diseased tissue based on a Raman-tagging approach.

As indicated above, cancerous tumors exhibit an acidic micro-environment, largely due to the glycolytic metabolic processes exhibited by cancer cells. More specifically, cancer cells generally exist in an acidic microenvironment having a pH of 6.4 to 6.8, whereas normal tissue typically exists in a neutral pH environment; i.e., a pH close to 7.2. To maintain the rapid growth and proliferation associated with tumor progression and tumor metastasis, cancer cells have a greater need for energy which is to a large degree fulfilled by an increased dependence on alternate metabolic pathways. Under aerobic conditions, cancer cells metabolize glucose to lactic acid. Studies have shown that the pH in the vicinity of the plasma membrane of cancer cells is about 0.3-0.7 pH units lower than the bulk extracellular pH. Thus, cancer cells have been be described as having a "crown of acidity" near their cell surfaces (e.g., See [21]). The bulk extracellular pH of tumor tissue generally correlates with perfusion, while the surface pH of cancer cells is expected to be less dependent on tumor tissue perfusion, and to be a predictive marker of tumor development and progression, since more aggressive tumor cells are more acidic.

Figure 1:
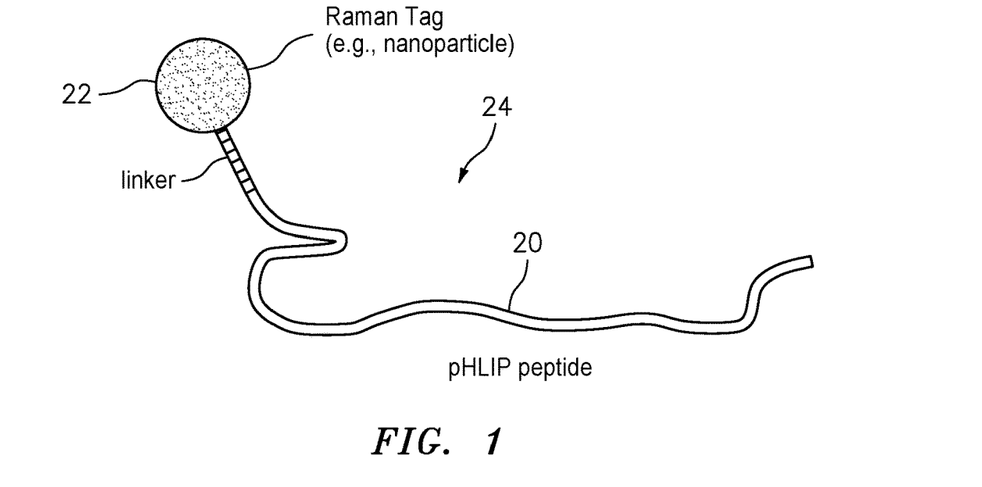
FIG. 1 is a diagrammatic illustration of a pH low insertion peptide (pHLIP) with a linked Raman reporter (RR).
Figure 2:
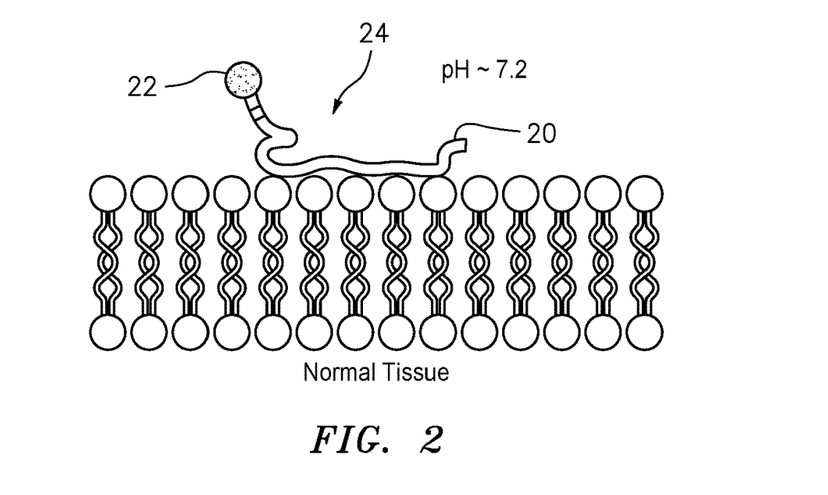
FIG. 2 is a diagrammatic illustration of a RR including a pHLIP interacting with a cell membrane at neutral pH.
Figure 3:
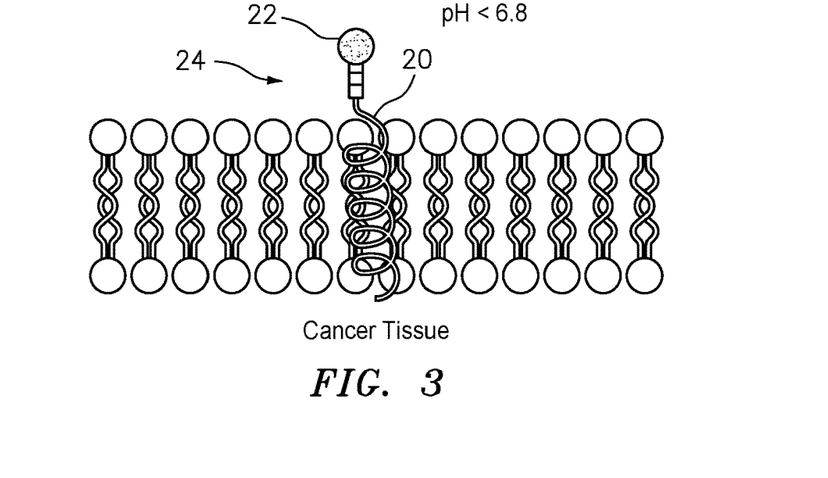
FIG. 3 is a diagrammatic illustration of a RR attached to a pHLIP interacting with a cell membrane in a slightly acidic environment (pH<7.0), with the pHLIP formed as a transmembrane alpha-helix inserting into the cell membrane.

Referring to FIGS. 1-3, the present disclosure utilizes pH sensing peptides called pH (low) insertion peptides 20 ("pHLIPs") as a means of targeting/identifying cancer cells. The term "pHLIP" as used herein refers to its common application (i.e., generically referring to pH (low) insertion peptides) and not to any particular peptide produced by any particular source. Moreover, the present disclosure may utilize a variety of different pHLIPs 20 and is, therefore, not limited to any particular type of pHLIP. pHLIPs are water-soluble membrane peptides that interact weakly with a cell membrane at neutral pH (e.g., see FIG. 2), but in a slightly acidic environment (pH<7.0) are capable of inserting into a cell membrane and forming a stable transmembrane alpha-helix (e.g., see FIG. 3); e.g., See [21], [32].

A pHLIP, or other peptide that that is configurable in a non-binding form when disposed in a neutral pH environment and configurable in a binding form when disposed in an acidic environment, that is configured to produce a Raman signature that is identifiable and distinguishable from Raman spectra produced by local endogenous materials may be referred to herein as a peptide component.

Figure 4:
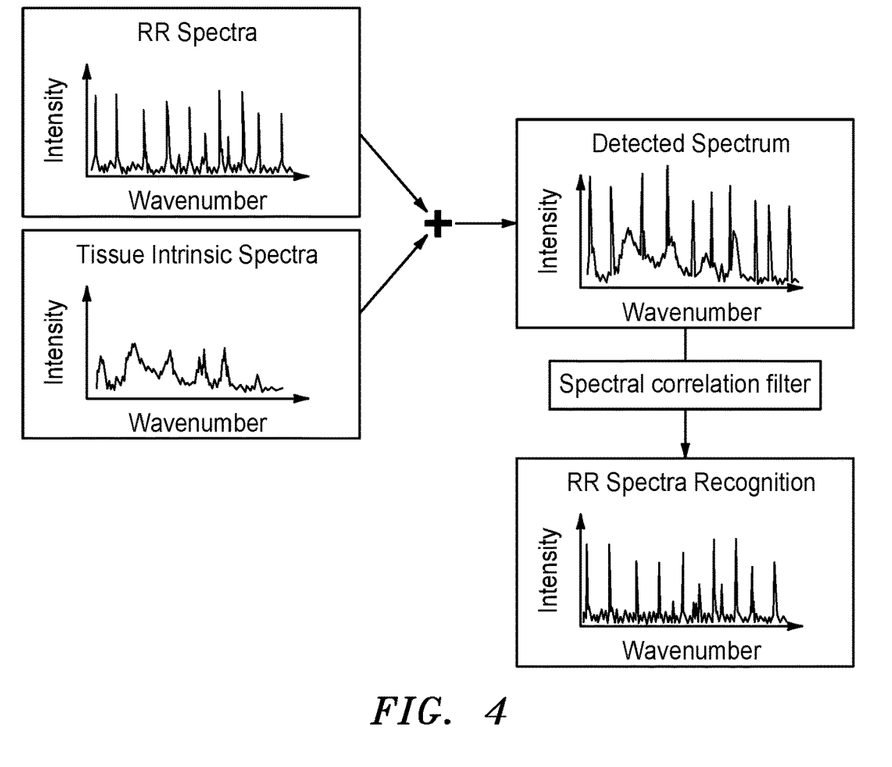
FIG. 4 diagrammatically illustrates Raman spectrum associated with a RR, Raman spectrum intrinsically associated with tissue, detected Raman spectrum which is a combination thereof, and how the Raman spectrum may be processed for recognition via a spectral correlation filter.

Embodiments of the present disclosure utilize pHLIPs 20 to "tag" cancerous tissue with a substance having a Raman signature that is identifiable, and that can be distinguished from local tissue Raman signals. For example, a Raman reporter ("RR") 22 may be conjugated with a pHLIP 20 (collectively referred to as a "RR-pHLIP" 24) to create a vehicle for selectively delivering the RR 22 to the cancerous tissue, thereby facilitating identification of the location and geometry of the tissue cancerous mass. RRs 22 comprise one or more molecules often called a "Raman dye" that upon exposure to incident light at predetermined wavelengths will produce Raman scattered light with a distinct and readily identifiable signature/spectrum. FIG. 4 illustrates a Raman spectrum intrinsically associated with tissue and an exemplary 'comb-like' or 'code-like' Raman spectrum from an RR 22, and the overall detected spectrum which is a combination thereof. FIG. 4 also illustrates how the detected spectra can be processed via a spectral correlation filter to selectively detect and analyze the spectrum associated with the RR 22. The spectral correlation filter (or similar device) can be used in those instances where the Raman spectrum of an RR 22 and the tissue intrinsic Raman spectrum overlap and reside in the same spectral region. In this manner, the RR 22 signature can be detected in the presence of otherwise interfering Raman signatures of the endogenous biospecies present, or other effects such as calcifications that commonly occur in tumors (e.g., see [0023]).

Figure 5:
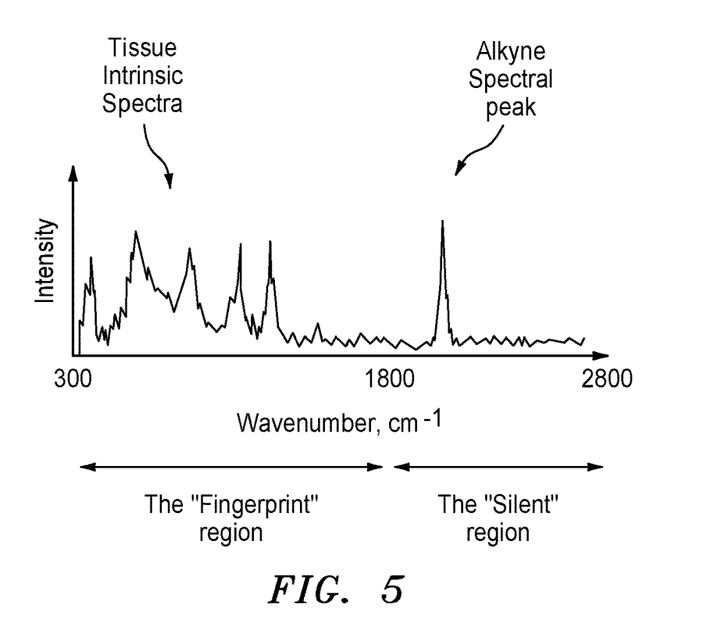
FIG. 5 represents a graph of Raman spectral intensity versus wavenumber, illustrating a "fingerprint region" and a "silent region".
Figure 6:
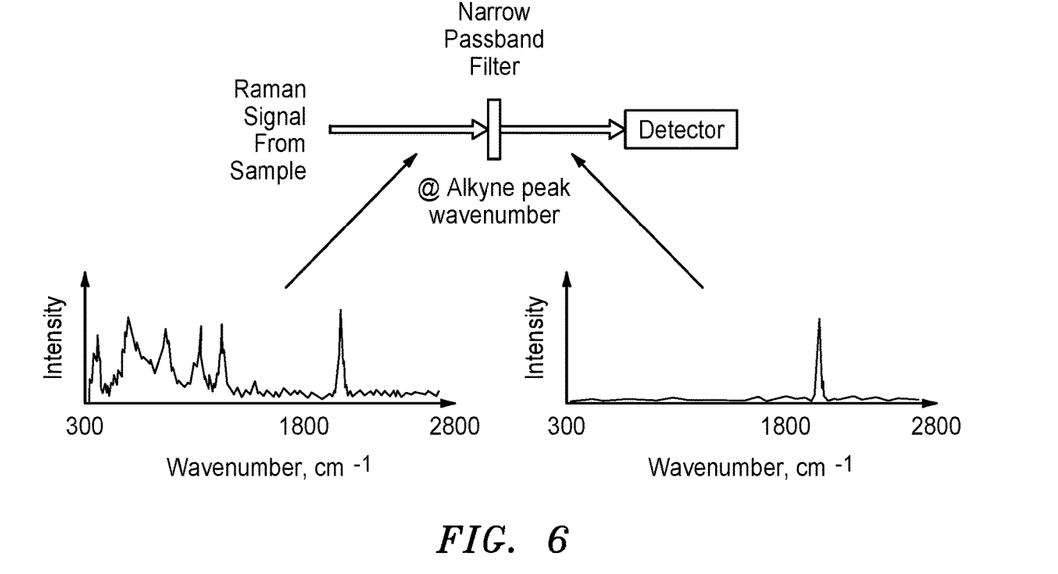
FIG. 6 diagrammatically represents a 'spectrometer-less' configuration of the current disclosure. The narrow band pass filter uniquely passes the Raman spectral signature of an RR-pHLIP configured to produce a Raman spectrum in the Raman silent region on to a simple detector. The spectrum on the left is similar to that shown in FIG. 5, and the other spectrum is primarily associated with an RR-pHLIP configured to produce a Raman spectrum in the Raman silent region.

Referring to FIGS. 5 and 6, in some exemplary embodiments of the present disclosure, RRs 22 may be configured to produce a Raman spectrum in the 'Raman silent region' where the Raman spectra of endogenous biospecies (e.g., non-cancerous and/or cancerous tissue intrinsic Raman spectra, including Raman spectra associated with tissue calcifications, etc.) are typically negligible. For example, an RR 22 may include an alkyne, a nitrile, or an azide moiety, or the like, or a compound containing such molecular sub-groups, such as EdU (5-ethynyl-2'-deoxyuridine) (e.g., see [0033]) bonded to the surface of a nanoparticle to produce a Raman spectrum in the Raman silent region. As will be described below, some RR 22 embodiments may be configured with a Surface Enhanced Raman Spectroscopic ("SERS") substrate material that enhances Raman signals. To be clear, an RR 22 may be configured to produce a Raman spectrum in the 'Raman silent region' with or without a SERS configuration. Alternatively, an alkyne, nitrile, or azide (or similar) moiety may be "linked" to a pHLIP 20, thereby obviating the need for an independent RR 22. The term "linked" as used here refers to any mechanism that permits the moiety or compound that produces a Raman spectrum in the Raman silent region to be connected with, or be incorporated as a part of, a pHLIP 20. As a non-limiting example, and as described below, pHLIPs 20 may be synthesized with amino acids that contain alkyne or other functional groups built into the pHLIP chain. Alkyne (a carbon-carbon triple bond) exhibits strong and characteristic peaks in the Raman silent region (typically about 1800 $cm^{-1}$ to 2800 $cm^{-1}$). The depiction within FIG. 5 of tissue intrinsic Raman spectra within both the fingerprint and silent regions, and Alkyne spectral peak within the silent region illustrates well the significance of utilizing a RR 22 that produces a Raman spectrum within the silent region. In the silent region the tissue intrinsic Raman spectra is negligible relative to the Alkyne spectral peak, and consequently the identification of the RR 22 Raman spectrum is significantly enhanced. Furthermore, it has been discovered that utilizing an RR 22 that produces a Raman spectrum within the silent region can also simplify the means of detection. For example, some embodiments of the present disclosure may utilize a narrow-pass band filter(s) that processes only Raman spectral peak signal(s) associated with the Raman signature of the RR in the Raman silent region (e.g., See FIG. 6); i.e., the narrow-pass band filter(s) permit passage of only those signals representative of the one or more Raman spectral peaks within the Raman silent region. This facile filter-based detection approach facilitates an elegant Raman "imaging" system that may use a light detector 32 without the need for a spectrometer or other spectral analysis device.

In some alternative embodiments, in addition to carbon-carbon or carbon-nitrogen triple bonds, the C—H frequency of Alkyne/Nitrile may be used to report the presence and concentration of an Alkyne/Nitrile moiety. In some embodiments, Polyethylene glycol (PEG) containing an Alkyne moiety could be coated or otherwise attached to a nanoparticle surface. The Alkyne moiety can either be a known molecular entity or a conjugated system either with a fluorophore, DNA or any other molecular species which can act as a secondary/surrogate marker.

In some exemplary embodiments of the present disclosure, an RR 22 may be configured with a Surface Enhanced Raman Spectroscopic ("SERS") substrate material with one or more Raman dye molecules attached/adsorbed to the substrate surface. This substrate material is typically a metallic material, and most often takes the form of a nanoparticle or nanostructure including nanostars. Upon light interrogation, a SERS substrate material provides Raman spectra response that is greatly enhanced (e.g., See [0024]-[0029]). SERS modified RRs 22 according to the present disclosure (e.g., RR-pHLIPs 24) provide a Raman spectra response greatly enhanced relative to a Raman spectra response produced by intrinsic biospecies. The enhancement effects of a Raman signal is generally attributed due to the excitation of localized surface plasmons, or chemical charge transfer, or some combination thereof. The SERS effect has been demonstrated in metals such as gold (Au) and silver (Ag), as well as platinum (Pt), ruthenium (Ru), palladium (Pd), iron (Fe), cobalt (Co), nickel (Ni), lithium (Li), sodium (Na), potassium (K), rubidium (Rb), copper (Cu), and the like. However, the SERS enhancement effect is much stronger for particles comprising a plasmonic material (e.g., noble metal, such as Au, Ag, etc.), or alkali metals (e.g., Li, Na, K, Rb, etc.), or certain base metals (e.g., Cu, etc.), or combinations or variants thereof. In some instances, an RR 22 may include novel materials such as graphene or other 2D materials that may form the basis of a SERS substrate. The present disclosure is not limited to using any particular SERS material.

In the exemplary embodiments of the present disclosure described above, pHLIPs 20 are used to "tag" cancerous tissue with a substance (e.g., an RR 22) having a Raman spectra signature that is identifiable, and distinguishable from the intrinsic Raman spectra produced by both the cancerous and non-cancerous tissue. In some alternative embodiments of the present disclosure, a pHLIP 20 may also be engineered to contain one or more unique chromophores or one or more functional groups as an integral part of the peptide, which chromophore or functional group produces a Raman signature that is identifiable, and distinguishable from Raman spectra from cancerous and/or non-cancerous tissue. Hence, the pHLIP 20 itself is configured to both attach to the cancerous tissue and "tag" it with a Raman signature that is identifiable and distinguishable from local Raman spectra. For example, if the pHLIP 20 is synthesized using triple carbon bonds in amino acid complexes, the 'Alkyne' Raman signature will be seen directly from the pHLIP 20 becoming associated with the cancerous cells. In these alternative embodiments, no separate conjugation/attachment of pHLIP 20 and a Raman reporter is required.

Figure 7:
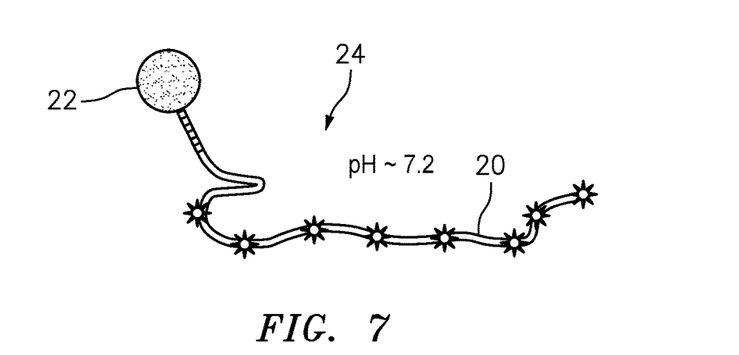
FIG. 7 illustrates schematic of pHLIP in an unfolded state, the unfolded pHLIP engineered to produce a first Raman signature.
Figure 8:
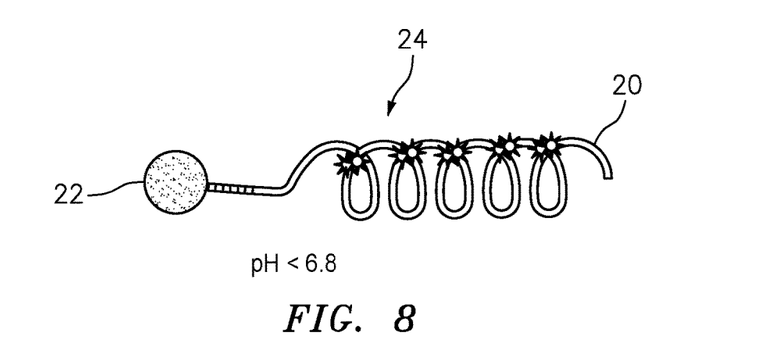
FIG. 8 illustrates schematic of pHLIP in a folded state (e.g., a helix configuration), the folded pHLIP engineered to produce a second Raman signature.

In some alternative embodiments of the present disclosure, a pHLIP 20 may also be engineered to produce a first Raman signature in its unfolded state (e.g., See FIG. 7) and to produce a second Raman signature in its folded state (e.g., See FIG. 8), which second Raman signature is distinguishable from the first Raman signature. In some instances, the change in Raman signature may be attributable to changes in the pHLIP 20 structure between the unfolded state and the folded state. The use of Raman spectroscopy to monitor structural changes in proteins and peptides has been reported (e.g., See [30], [31]).

In some embodiments of the present disclosure, additional cancer cell tagging mechanisms may be utilized. Non-limiting examples of such tagging mechanisms include antibodies (Ab) that target certain protein biomarkers on cell membranes; e.g., EGFR, RAS, HER2/Neu biomarkers. These additional cancer cell tagging mechanisms may be utilized in combination with additional specific RR-antibody combinations and the pHLIPs 20 used to "tag" cancerous tissue with a substance having a Raman signature that is identifiable and distinguishable from Raman spectra from both the cancerous and non-cancerous tissue. The combination of the antibody tagging mechanisms and the pHLIPs 20 with an identifiable/distinguishable Raman signal may be used to provide additional verification of the presence or absence of cancerous tissue, and/or to provide identification of one or more specific types of cancers.

Figure 9:
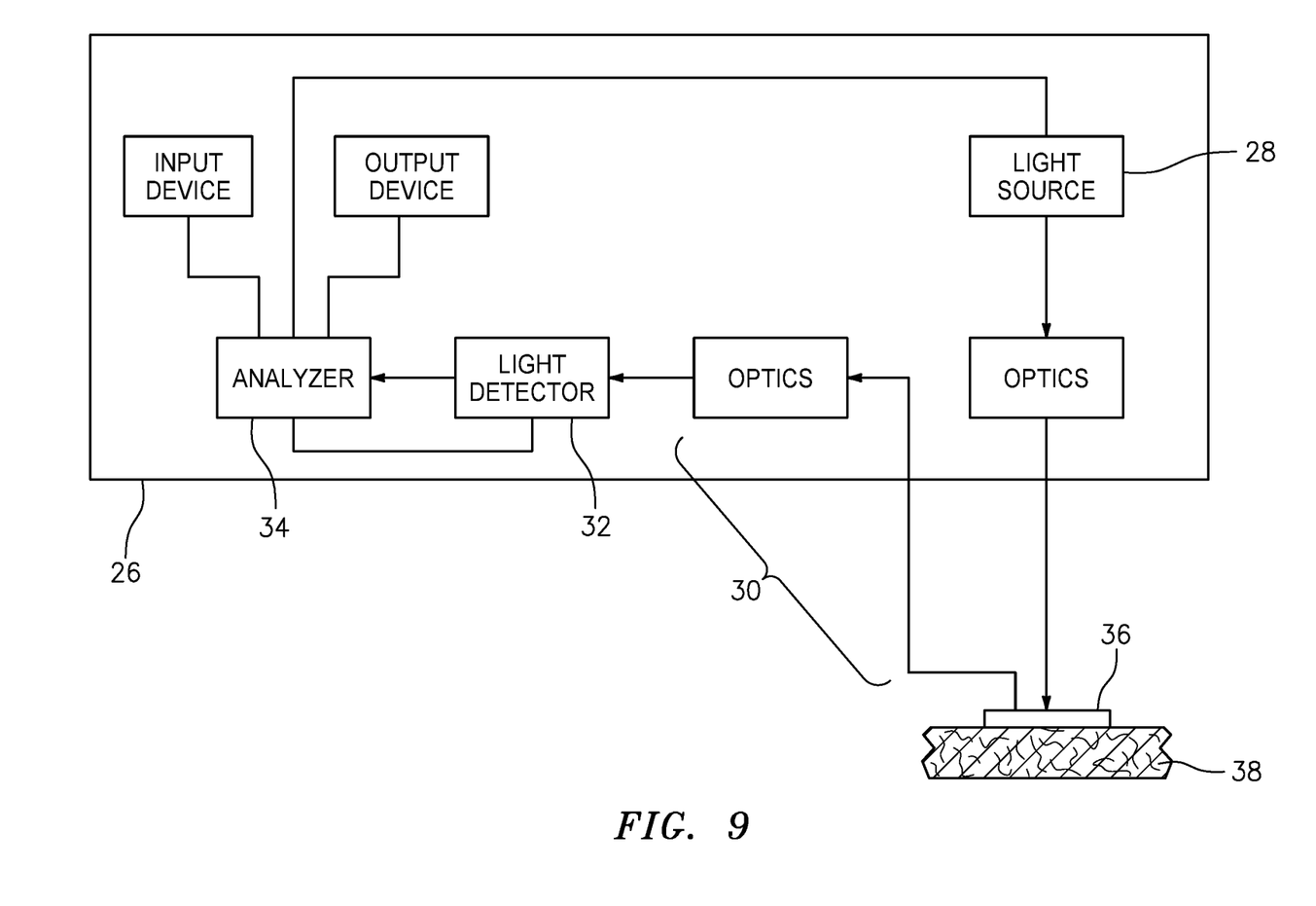
FIG. 9 is a diagrammatic illustration of present disclosure system.

Referring to FIG. 9, a diagrammatic illustration of a present disclosure system 26 exemplary embodiment is shown. The aforesaid system 26 embodiment includes a plurality of components. The system 26 embodiments include at least one light source 28, collection light optics 30, at least one light detector 32, and an analyzer 34. In some embodiments, the system 26 may include a tissue interface device 36. As will be described herein, the configuration of these components may vary in different system 26 embodiments. The system 26 embodiment description provided herein may refer to various different system 26 components as independent components. The present disclosure is not limited to specific descriptions provided herein. For example in alternative embodiments, system 26 components may be combined, or arranged in a different manner than that shown in the Figures, and still be within the scope of the present disclosure.

The light source 28 is configured to emit coherent light. An example of an acceptable coherent light source 28 is a laser. A variety of different lasers may be used within the system 26, and the present disclosure is not therefore limited to using any particular laser. Examples of laser types include solid state, gas, diode laser or vertical-cavity surface-emitting lasers (VCSELs). The present disclosure may utilize coherent light at a variety of different wavelengths, and the light source 28 is therefore not limited to coherent light at any particular wavelength or wavelength band.

The light source 28 is not limited to any particular incident beam configuration/illumination such as point, line, light-sheet or full-field illumination. The incident beam produced by the light source 28 is configured to adequately illuminate tissue specimen over the surface where cancerous tissue may be present.

Light from the light source 28 may be transferred from the light source 28 to the subject tissue 38 (see FIG. 9) via optical fibers, and may be conditioned by optics (e.g., lenses, filters, etc.). The light from the light source 28 may be oriented at multiple angles relative to the subject tissue 38 using a tissue interface device 36 to facilitate interrogation of the subject tissue.

The collection light optics 30 are configured to transfer, and in some instances process, light emitted from the interrogated tissue; e.g., Raman scattered light emitted from the tissue as a result of incident light interrogation. The collection light optics 30 may include one or more lenses, filters, dichroic mirrors, and the like for processing the received light into a desirable form. The filters are not limited to optical filters and a filter can be any molecular system or device such as electronically-tunable acousto-optical filter as a wavelength selector. As indicated above, the filters may include one or more narrow-pass band filter(s) configured to process only wavelengths associated with defined Raman spectra peaks associated with those of the RRs used. For example, in the case of an Alkyne RR, the Raman signatures of interest are found within the Raman silent region (e.g., about 1800 $cm^{-1}$ to 2800 $cm^{-1}$).

Figure 10:
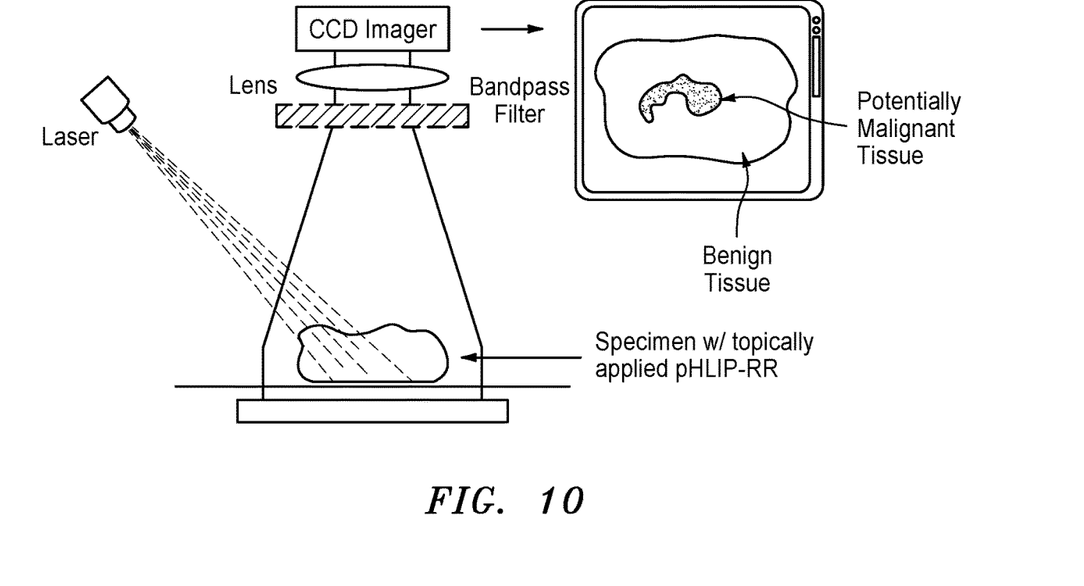
FIG. 10 is a diagrammatic illustration of an imaging system based on the present disclosure.

The at least one light detector 32 is configured to receive light (e.g., Raman spectra) emitted from the interrogated tissue via the collection light optics 30 and produce signals representative thereof. The signals produced by the light detector 32 are transferred to the analyzer 34. Non-limiting examples of light detectors 32 include light sensors that convert light energy into an electrical signal such as a simple photodiode, or other optical detectors of the type known in the art, such as CCD arrays. In some embodiments, particularly those involving the use of fibers or fiber bundles to convey the light from the subject tissue to the detectors, a charge couple device (CCD) or CMOS cameras may be used. In this case, the fibers may be arranged to fall onto an individual pixel, or groups of CCD pixels which would be 'binned' into a single output. In this case a large format bandpass filter could be used to select the RR spectral feature/peak onto the CCD pixels. An exemplary configuration is illustrated in FIG. 10. Here, the tissue sample is illuminated by a laser signal that diverges to cover the spatial area of the tissue sample. Light emitted from the tissue sample (as a result of the laser light application) is then imaged onto a light detector (e.g., a CCD imager/camera). A bandpass optical filter positioned ahead of the CCD can be used to allow only the RR 22 spectral features to be passed to the detector. In the case of the use of an Alkyne RR 22, the spectral features (e.g., peak) would be positioned at a wavenumber in the silent region of the Raman spectrum, and thus provides very high discrimination against other interfering Raman and fluorescence signatures.

The analyzer 34 is in communication with other components within the system 26, such as the light source 28, the light detector 32, and the like to control and/or receive signals therefrom to perform the functions described herein. The analyzer 34 may include any type of computing device, computational circuit, processor(s), CPU, computer, or the like capable of executing a series of instructions that are stored in memory. The instructions may include an operating system, and/or executable software modules such as program files, system data, buffers, drivers, utilities, and the like. The executable instructions may apply to any functionality described herein to enable the system 26 to accomplish the same algorithmically and/or coordination of system 26 components. The analyzer 34 may include a single memory device or a plurality of memory devices. The present disclosure is not limited to any particular type of non-transitory memory device, and may include read-only memory, random access memory, volatile memory, non-volatile memory, static memory, dynamic memory, flash memory, cache memory, and/or any device that stores digital information. The analyzer 34 may include, or may be in communication with, an input device that enables a user to enter data and/or instructions, and may include, or be in communication with, an output device configured, for example to display information (e.g., a visual display or a printer), or to transfer data, etc. Communications between the analyzer 34 and other system 26 components (e.g., the light source 28, light detector 32, etc.) may be via a hardwire connection or via a wireless connection.

The following description provides an illustration of how the present disclosure system and methodology may be utilized to determine the presence or absence of cancerous cells (e.g., within any tissue body, including but not limited to breast tissue), and to determine boundaries (i.e., the tumor margin) between cancerous tissue and non-cancerous tissue.

Figure 11:
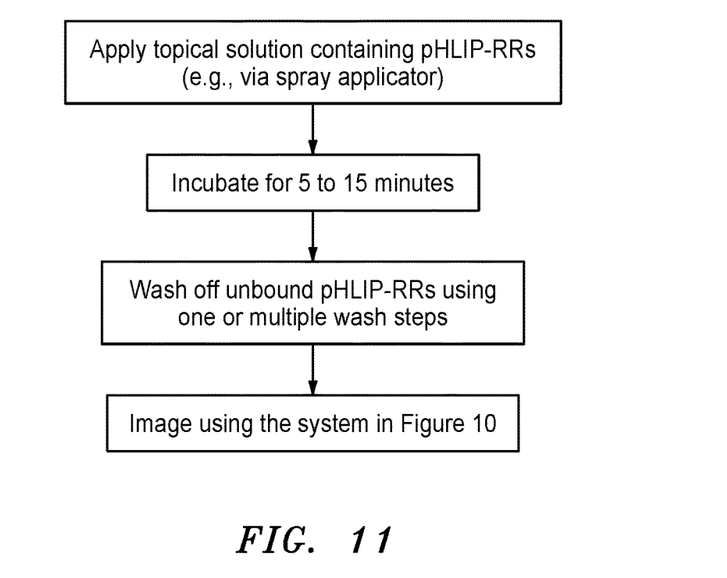
FIG. 11 is a flow chart illustrating exemplary steps for topical application of a solution to a tissue sample.

Under the present disclosure Raman-based system and methodology, if a clinician seeks to determine the presence or absence of cancerous tissue, the clinician may administer a material containing "Raman" pHLIPs 20 (e.g., RR-pHLIPs 24, pHLIPs linked with a moiety having a Raman signal in the silent region, or pHLIPs themselves configured to produce the aforesaid identifiable/distinguishable Raman signature, and combinations thereof as described above) to tag cancerous tissue with a Raman signature that is identifiable and distinguishable from Raman spectra produced by local endogenous materials. The material may be configured in different forms (e.g., a fluid, a solid, etc.) and may be administered in a variety of different ways (e.g., intravenously, topically, etc.). Within a period of time, the Raman pHLIPs provided within the material will disperse on or in the subject tissue. In the event cancer cells are present, some number of the Raman pHLIPs within the material will reside in an acidic environment produced on or in close proximity to the surface of each cancer cell. In that acidic environment, at least some of those Raman pHLIPs will form an alpha helix configuration that links the respective Raman pHLIP with a respective cancer cell. Those Raman pHLIPs not linked to cancer cells will either naturally purge from the subject's system over a determinable period of time or can be rinsed away using a wash solution (e.g., a buffer solution) if the material was topically applied. The flow chart in FIG. 11 describes exemplary steps for a topical application. The present disclosure is not limited to any particular mechanism for removing unlinked pHLIPs. After an 'incubation' period of time sufficient for the Raman pHLIPs to link with any cancer cells that may be present and for unbound Raman pHLIPs to be purged, the subject's tissue may be imaged using the present system 26.

The process of administering the material containing Raman pHLIPs to tag cancer cells with the described identifiable/distinguishable Raman signature, and the process of subjecting the suspected cells/tissue with light and collecting emitted light (i.e., "imaging") can be accomplished in a variety of different ways, and therefore the present disclosure is not limited to any particular material administration process, or any particular imaging process. For example if the suspect cells/tissue are in-vivo, the pHLIP material may be administered intravenously to the subject or by topical application directly to the suspect cells/tissue. The suspect in-vivo cells/tissue may be imaged in their in-vivo position using the present system to ascertain the presence of the pHLIP Raman signature indicative of cancerous cells. This imaging may provide accurate information regarding the position of cancerous tissue and concomitant tumor margin. Alternatively, in some applications it may be useful to first excise a suspected tissue mass, and subsequently image the excised tissue mass to ascertain the presence of the pHLIP Raman signature indicative of cancerous cells. In those applications where a suspected tissue mass has been excised, it may be useful to image the tissue regions surrounding the void where the now-excised suspect tissue mass previously resided to ascertain the presence of any pHLIP Raman signature within the remaining tissue. In applications where a suspected tissue mass has been excised, prior to imaging the tissue around the excised void, it may be useful to topically apply (or reapply) the pHLIP material to the tissue regions surrounding the void, after a meaningful period of time wash the aforesaid tissue to remove any unbound pHLIP Raman, and then image those tissue regions. In this manner, the present disclosure can be used to provide a meaningful determination regarding the presence of absence of cancerous cells in the tissue regions surrounding the void where the suspect tissue mass was excised.

The imaging of tissue using the present system (i.e., the process of subjecting the suspected cells/tissue with light and collecting Raman scattered light emitted from the tissue) includes collecting the emitted light and passing the collected light to one or more light detectors 32. As stated above, the emitted light may be collected by detector fibers, and the collected emitted light may be passed through collection light optics 30 prior to reaching the light detectors 32. The present disclosure is not limited to this arrangement, however; e.g., emitted light may pass though optical filters, and thereafter be directed to light detectors 32 via optical fibers.

The exemplary system embodiment shown in FIG. 10. Here the laser illumination is configured for wide-field illumination of, for example, an excised tumor specimen. The laser beam thus illuminates the whole specimen or a portion of the specimen of particular interest. The specimen, or portion thereof, is imaged using a CCD image/camera or other suitable imaging device as known in the art. A bandpass optical filter is positioned to receive collected emitted light prior to that collected light engaging the imaging device/camera. The bandpass optical filter may be a narrow-pass bandwidth filter that only permits passage of spectra in a narrow range of the Raman silent region. If Raman pHLIP of the type that produce a Raman signature in that range within the silent region (e.g., RR-pHLIPs 24 linked with a moiety such as Alkyne that produces a Raman signal in the silent region, or a pHLIP 20 linked with such a moiety, etc.) are administered to the suspect tissue and such Raman pHLIP are present within the imaged tissue, the spectra produced during imaging will engage the bandpass optical filter and only that spectra in the Raman silent region will pass through the filter. The aforesaid spectra is subsequently passed to the light detector 32 and to the analyzer 34. As stated above, Raman spectra produced by tissue and other abnormal conditions (e.g., calcifications) within the Raman silent region is negligible relative to the Raman spectra produced by Raman pHLIP having an alkyne or nitride moiety. Hence, Raman spectra produced by such a Raman pHLIP is clearly identifiable in the Raman silent region without the need for a spectrometer or other similar functioning device. If the presence of cancerous cells is determined, the present system 26 may be utilized to create a diagnostic image, such as a false color mapped image of the cancerous tissue mass/specimen. To facilitate this last step, the narrow-pass bandwidth filter may be configured such that it can be mechanically or electronically switched out of the field of view of the imaging device/camera to permit capture of a 'white-light' image (normal RGB or monochrome image) of the specimen onto which the false color information from the Raman image can be mapped, as illustrated in FIG. 10.

As stated above, during surgical procedures there is great clinical value in determining the boundary between normal tissue and cancerous tissue; i.e., the location of the tumor margin. The present system 26 may be utilized by a clinician to makes such a determination; e.g., by topical application of a solution containing pHLIPs 20 configured to "tag" cancerous tissue with a substance having a Raman spectral signature that is identifiable and distinguishable from local Raman spectra.

Figure 12:
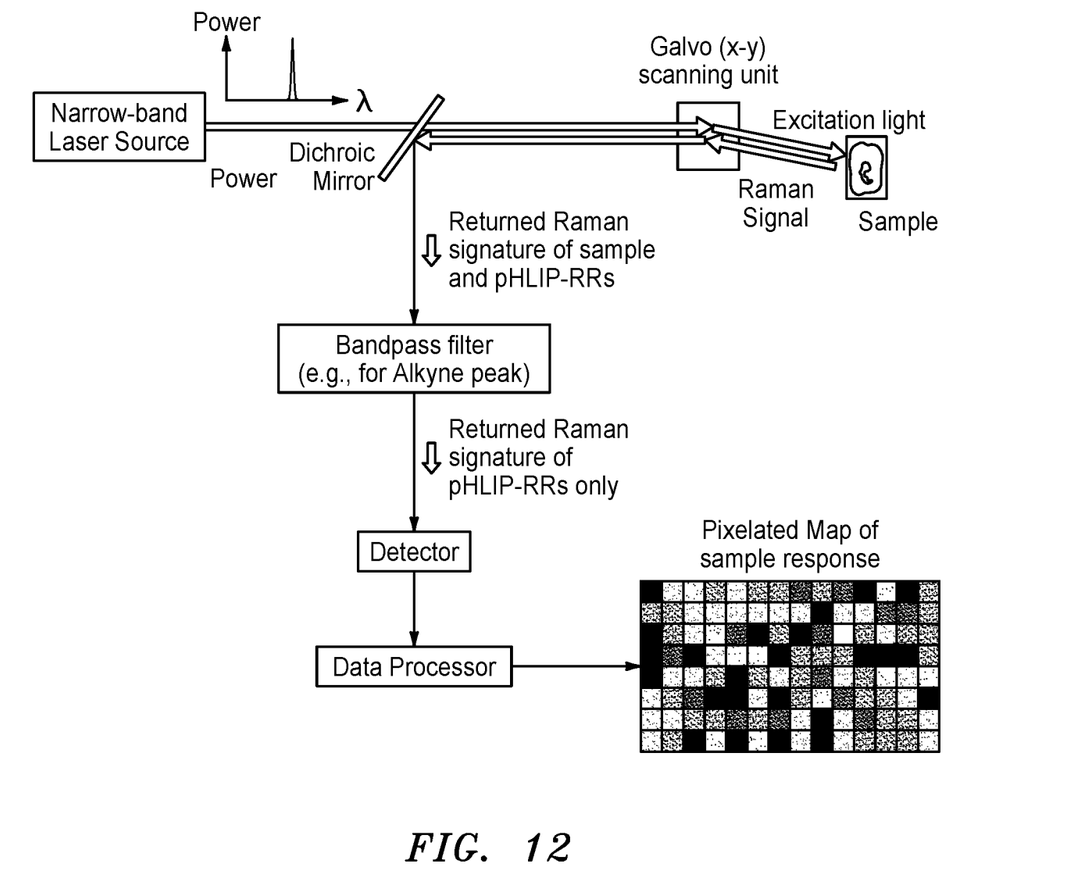
FIG. 12 is a diagrammatic representation of a system embodiment according to the present disclosure.

FIG. 12 illustrates an additional embodiment of the present system 26 in which a single point illumination of the excitation laser is used, and the detected light is passed to a single detector through a bandpass filter set to pass a RR 22 spectral feature. The single point of illumination and observation may be controlled by an X-Y scanner such as a galvo scanner, as known in the art, (or the tissue sample could be translated in the X-Y plane using an X-Y motion stage), such that the whole area of the sample, or portions thereof, could get scanned. This configuration eliminates the need of an imaging system, and allows the use of a single detector for creating a pixelated image of the specimen that indicates the Raman signals detected and this the presence of cancer.

It is noted that various connections are set forth between elements in the present description and drawings (the contents of which are included in this disclosure by way of reference). It is noted that these connections are general and, unless specified otherwise, may be direct or indirect and that this specification is not intended to be limiting in this respect. A coupling between two or more entities may refer to a direct connection or an indirect connection. An indirect connection may incorporate one or more intervening entities or a space/gap between the entities that are being coupled to one another.

Furthermore, any reference to singular includes plural embodiments, and any reference to more than one component or step may include a singular embodiment or step. Also, any reference to attached, fixed, connected or the like may include permanent, removable, temporary, partial, full and/or any other possible attachment option.

Furthermore, no element, component, or method step in the present disclosure is intended to be dedicated to the public regardless of whether the element, component, or method step is explicitly recited in the claims. No claim element herein is to be construed under the provisions of 35 U.S.C. 112(f) unless the element is expressly recited using the phrase "means for." As used herein, the terms "comprises", "comprising", or any other variation thereof, are intended to cover a non-exclusive inclusion, such that a process, method, article, or apparatus that comprises a list of elements does not include only those elements but may include other elements not expressly listed or inherent to such process, method, article, or apparatus.

Each of the following references is hereby incorporated by reference in its entirety.

REFERENCES

1. Nguyen and Tsien, "Fluorescence-guided surgery with live molecular navigation—a new cutting edge", Nat Rev Cancer, 13(9), pp. 653-662, 2013.
2. Tummers, et al., "Real-time intraoperative detection of breast cancer using near-infrared fluorescence imaging and methylene blue", Eur J Surg Oncol., 40(7), 850-858, 2014.
3. Dahr et al., "A diffuse reflectance spectral imaging system for tumor margin assessment using custom annular photodiode arrays", Biomedical Optics Express, 3, (12), 2012.
4. Harmsen et al., "Cancer imaging using surface-enhanced resonance Raman scattering nanoparticles", Nat Protoc.; 11(4): 664-87, 2016
5. Matousek et al., "Noninvasive Raman spectroscopy of human tissue in vivo," Appl. Spectrosc. 60(7), 758-763, 2006.
6. Mahadevan-Jansen, Richards-Kortum, "Raman spectroscopy for the detection of cancers and precancers", J Biomed Opt.; 1(1):31-70, 1996.
7. Talari, A. et al., "Raman Spectroscopy of Biological Tissues", Applied Spectroscopy Reviews, 50:1, 46-111, 2015.
8. Pence I., Mahadevan-Jansen A., "Clinical instrumentation and applications of Raman spectroscopy", Chem Soc Rev.; 45 (7):1958-1979, 2016.
9. Yaroslavsky. A, et al., "Delineating nonmelanoma skin cancer margins using terahertz and optical imaging", J of Biomedical Photonics & Eng., 3(1), 2017.
10. Ifa and Eberlin, "Ambient Ionization Mass Spectrometry for Cancer Diagnosis and Surgical Margin Evaluation", Clin Chem.; 62(1), 2016.
11. Zhang et al., "Nondestructive tissue analysis for ex vivo and in vivo cancer diagnosis using a handheld mass spectrometry system", Science Translational Medicine, 9, 2017.
12. Warburg, O., "On the origin of cancer cells", Science 123, pp. 309-314, 1956.
13. Gatenby et al., "Why do cancers have high aerobic glycolysis?", Nature Rev Cancer, 4, 891, 2004
14. Webb et al., "Dysregulated pH: a perfect storm for cancer progression", Nature Reviews. Cancer, 11, p 671, 2011
15. Andreev, et al., "pH-sensitive membrane peptides (pHLIPs) as a novel class of delivery Agents", Mol. Membr. Biol., 27, pp. 341-352, 2010
16. Adochite et al., "Targeting Breast Tumors with pH (Low) Insertion Peptides", Mol. Pharmaceutics, 11 (8), pp 2896-2905, 2014
17. Werakkoddy et al., "Novel pH-Sensitive Cyclic Peptides", Scientific Reports, 6, 2016.
18. Korzeniowska et al., "Intracellular pH-sensing using core/shell silica nanoparticles", J Biomed Nanotechnol., 10(7), pp. 1336-45, 2014
19. Tsuchikama and An, "Antibody-drug conjugates: recent advances in conjugation and linker chemistries", Protein Cell, 9, pp. 33-46, 2018.
20. Demoin, et al. PET imaging of extracellular pH in tumors with 64Cu— and 18F-labeled pHLIP peptides: A structure-activity optimization study. Bioconjugate Chem. 2016; 27:2014-2023.
21. Wyatt et al., Applications of pHLIP Technology for Cancer Imaging and Therapy, Trends Biotechnol. 2017 July, 35(7): 653-664
22. Keller M. D. et al., "Spatially offset Raman spectroscopy of layered soft tissues", Opt Lett., 34(7): 926-8, 2009.
23. Stone et al., "Subsurface probing of calcifications with spatially offset Raman spectroscopy (SORS): future possibilities for the diagnosis of breast cancer", Analyst; 132(9): pp. 899-905 2007.
24. Qian X, et al. In vivo tumor targeting and spectroscopic detection with surface-enhanced Raman nanoparticle tags. Nat Biotechnol. 2008; 26: 83-90

25. Chrysafis et al., "Surface-Enhanced Raman Spectroscopy: A New Modality for Cancer Imaging" J Nucl Med.; 56(9): 1295-1299, 2015.
26. Dinish et al., "Actively targeted in vivo multiplex detection of intrinsic cancer biomarkers using biocompatible SERS nanotags", Sci Rep.; 12, 4:4075, 2014.
27. Antosh M P, et al. Enhancement of radiation effect on cancer cells by gold-pHLIP. Proc Natl Acad Sci USA; 112: pp. 5372-5376, 2015.
28. Yao L, et al. pHLIP peptide targets nanogold particles to tumors. Proc Natl Acad Sci USA; 110:465-470, 2013.
29. Yu et al, "A pH-Driven and photoresponsive nanocarrier: Remotely-controlled by near-infrared light for stepwise antitumor treatment", Biomaterials; 79: pp. 25-35, 2016.
30. Shashilov et al., "Quantitative methods for structural characterization of proteins based on deep UV resonance Raman spectroscopy", Methods; 52 (1), pp. 23-37, 2010.
31. Brown et al., "Bilayer surface association of the pHLIP peptide promotes extensive backbone desolvation and helically-constrained structures", Biophysical Chemistry; 187-188, pp. 1-6, 2014.
32. "pHLIP (pH Low Insertion peptide) Technology for Cancer Diagnosis and Treatment", Internet article at www.biophys.phys.uri.edu/pHLIP.html, Aug. 22 2019
33. Jamieson et al., "Tracking intracellular uptake and localization of alkyne tagged fatty acids using Raman spectroscopy", Spectrochimica Acta Part A: Molecular and Biomolecular Spectroscopy 197, pp. 30-36 (2018).

The invention claimed is:

1. A method for determining the presence or absence of cancerous cells within subject tissue, the method comprising:
   providing a material that includes at least one type of peptide component configurable in a non-binding form when disposed in a neutral pH environment, and in a binding form when disposed in an acidic pH environment, wherein the peptide component is configured to produce a first Raman spectrum when subjected to one or more predetermined wavelengths of light;
   wherein the peptide component includes a pH (low) insertion peptide (pHLIP) and a Raman Reporter (RR), the RR configured to produce the first Raman spectrum when subjected to the one or more predetermined wavelengths of light, and the first Raman spectrum is distinguishable from Raman spectra produced by the subject tissue when subjected to the one or more predetermined wavelengths of light; and
   wherein the first Raman spectrum resides within a Raman silent region defined by a wavelength region within a range of about 1800 $cm^{-1}$ to about 2800 $cm^{-1}$;
   administering the material to a subject tissue and allowing the material to reside with the subject tissue for an incubation period of time;
   washing the subject tissue after the incubation period to remove any unbound peptide components;
   interrogating the subject tissue with light at the one or more predetermined wavelengths of light produced by one or more light sources after the subject tissue has been washed after the incubation period;
   sensing the subject tissue for light emitted from the subject tissue using one or more light detectors, the emitted light resulting from the light interrogation of the subject tissue, and producing signals representative of the sensed emitted light;
   analyzing the signals representative of the sensed emitted light using an analyzer to determine a presence or absence of the first Raman spectrum produced by the peptide component when subjected to one or more predetermined wavelengths of light; and
   determining the presence or absence of cancerous cells within the subject tissue based on the presence or absence of the first Raman spectrum within the sensed light emitted from the subject tissue.

2. The method of claim 1, wherein the RR includes at least one of an alkyne, a nitrile, or an azide moiety.

3. The method of claim 1, wherein the step of sensing the subject tissue for light emitted from the subject tissue using one or more light detectors, includes filtering the signals representative of the sensed emitted light through one or more narrow-pass band filters configured to permit passage of only those signals representative of the first Raman spectrum within the Raman silent region.

4. The method of claim 3, wherein the steps of sensing and analyzing are performed without a spectral analysis device.

5. The method of claim 1, wherein the RR includes at least one surface enhanced Raman spectroscopic (SERS) material.

6. The method of claim 1, wherein the pHLIP is configurable in the non-binding form or the binding form, and in the binding form the pHLIP produces the first Raman spectrum when subjected to one or more predetermined wavelengths of light.

7. A system for determining the presence or absence of cancerous cells within subject tissue, the system comprising:
   a material that includes at least one type of peptide component configurable in a non-binding form when disposed in a neutral pH environment, and in a binding form when disposed in an acidic pH environment, wherein the peptide component is configured to produce a first Raman spectrum when subjected to one or more predetermined wavelengths of light;
   wherein the peptide component includes a pH (low) insertion peptide (pHLIP) and a Raman Reporter (RR), the RR configured to produce the first Raman spectrum when subjected to the one or more predetermined wavelengths of light, and the first Raman spectrum is distinguishable from Raman spectra produced by the subject tissue when subjected to the one or more predetermined wavelengths of light, and wherein the first Raman spectrum resides within a Raman silent region defined by a wavelength region within a range of about 1800 $cm^{-1}$ to about 2800 $cm^{-1}$;
   at least one light source configured to interrogate a subject tissue with light at the one or more predetermined wavelengths of light;
   at least one light detector configured to detect light emitted from the subject tissue, the emitted light resulting from the light interrogation of the subject tissue, and configured to produce signals representative of the detected emitted light;
   one or more narrow-pass band filters configured to permit passage limited to the signals representative of the detected emitted light that are also representative of the first Raman spectrum within the Raman silent region; and
   an analyzer in communication with the at least one light source, the at least one light detector, and a non-transitory memory storing instructions, which instructions when executed cause the analyzer to:

control the at least one light source to interrogate subject tissue with the light at the one or more predetermined wavelengths of light, the subject tissue administered with the material;

receive the signals representative of the detected emitted light that are representative of the first Raman spectrum within the Raman silent region from the one or more narrow-pass band filters;

analyze the signals representative of the first Raman spectrum within the Raman silent region to determine a presence or absence of the first Raman spectrum; and determine the presence or absence of cancerous cells within the subject tissue based on the presence or absence of the first Raman spectrum within the sensed light emitted from the subject tissue.

8. The system of claim 7, wherein the RR includes at least one of an alkyne, a nitrile, or an azide moiety.

9. The system of claim 7, wherein the analyzer is configured to determine the presence or absence of cancerous cells within the subject tissue without a spectral analysis device based on the presence or absence of the first Raman spectrum within the sensed light emitted from the subject tissue.

10. The system of claim 7, wherein the RR includes at least one surface enhanced Raman spectroscopic (SERS) material.

11. The system of claim 7, wherein the pHLIP is configurable in the non-binding form or the binding form, and in the binding form the pHLIP produces the first Raman spectrum when subjected to one or more predetermined wavelengths of light.

12. The method of claim 5, wherein the at least one surface enhanced Raman spectroscopic (SERS) material includes at least one of gold, silver, platinum, ruthenium, palladium, iron, cobalt, nickel, lithium, sodium, potassium, rubidium, or copper.

13. The system of claim 10, wherein the at least one surface enhanced Raman spectroscopic (SERS) material includes at least one of gold, silver, platinum, ruthenium, palladium, iron, cobalt, nickel, lithium, sodium, potassium, rubidium, or copper.

* * * * *